ately after page load.

United States Patent [19]
Whitney

[11] Patent Number: 4,472,422
[45] Date of Patent: Sep. 18, 1984

[54] ANTIHYPERTENSIVE 4,5-DIARYL-α-POLYFLUORO-ALKYL-1H-IMIDAZOLE-2-METHANAMINES

[75] Inventor: Joel G. Whitney, Kennett Square, Pa.

[73] Assignee: E. I. Du Pont de Nemours and Company, Wilmington, Del.

[21] Appl. No.: 506,605

[22] Filed: Jun. 24, 1983

Related U.S. Application Data

[63] Continuation-in-part of Ser. No. 471,270, Mar. 2, 1983, abandoned.

[30] Foreign Application Priority Data

Sep. 6, 1982 [ZA] South Africa .................. 82/006501

[51] Int. Cl.³ ..................... A01N 43/40; A01N 43/50
[52] U.S. Cl. ................................. 424/273 R; 424/263
[58] Field of Search ........................... 424/263, 273 R

[56] References Cited

U.S. PATENT DOCUMENTS

| | | | |
|---|---|---|---|
| 4,058,612 | 11/1977 | Neustadt | 424/251 |
| 4,159,338 | 6/1979 | Cherkofsky et al. | 424/273 R |
| 4,182,769 | 1/1980 | Cherkofsky et al. | 424/273 R |
| 4,190,666 | 2/1980 | Cherkofsky et al. | 424/274 |
| 4,348,404 | 9/1982 | Whitney | 424/263 |

FOREIGN PATENT DOCUMENTS

2093031  8/1982  United Kingdom .

OTHER PUBLICATIONS

Friedman, Systolic Blood Pressure in the Rat, Proc. Soc. Exp. Biol. & Med., vol. 70, 670 (1949).
Wentworth, Polyfluorodiazo Compounds, J. Org. Chem., vol. 32, 3197 (1967).

*Primary Examiner*—Allen J. Robinson

[57] ABSTRACT

4,5-Diaryl-α-polyfluoroalkyl-1H-imidazole-2-methanamines are useful in the treatment of hypertension.

9 Claims, No Drawings

ANTIHYPERTENSIVE 4,5-DIARYL-α-POLYFLUORO-ALKYL-1H-IMIDAZOLE-2-METHANAMINES

RELATED APPLICATION

This application is a continuation-in-part of copending application U.S. Ser. No. 471,270, filed Mar. 2, 1983 now abandoned.

BACKGROUND OF THE INVENTION

This invention relates to the use of diaryl imidazoles to treat hypertension.

Numerous antihypertensive agents are known in the art. For example, U.S. Pat. No. 4,058,612 discloses 6-(polyhaloisopropyl)quinazoline-2,4-diones and U.K. Pat. No. 2,093,031 discloses 4-aroylimidazole-2-ones that have antihypertensive properties. There is nevertheless a continuing need for additional antihypertensive agents because of the various side effects which can occur with existing agents.

SUMMARY OF THE INVENTION

According to the present invention, there is provided a method of treating hypertension in a mammal which comprises administering to the mammal an effective antihypertensive amount of a compound of Formula I:

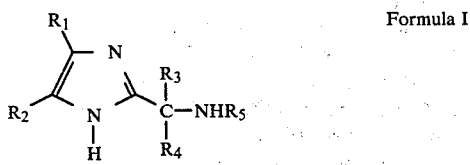

Formula I wherein $R_1$ and $R_2$ independently are 2-pyridyl, 3-pyridyl, 4-pyridyl or

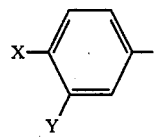

where
$X = H$, F, Cl, Br, $C_1-C_2$ alkyl, $C_1-C_2$ alkoxy, di($C_1-C_2$ alkyl)amino, ($C_1-C_2$ alkyl)S(O)$_n$, or $NO_2$, where $n = 0$, 1 or 2;
$Y = H$, F or Cl; provided when $Y = F$ or Cl, then $X$ must be F or Cl;
further provided that (1) one of $R_1$ and $R_2$ must be

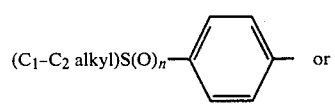 or

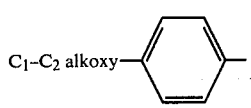, and (2) only one of $R_1$ and $R_2$ can be selected from the group consisting of 2-pyridyl, 3-pyridyl, 4-pyridyl,

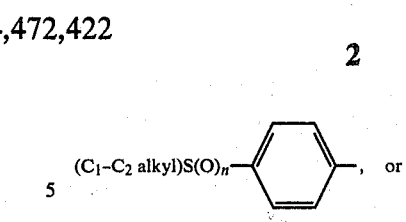, or

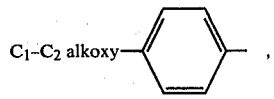, $R_3$ and $R_4$ independently = $CF_3$, $CF_2H$, $CF_2Cl$, $CFCl_2$ or $CF_2CF_3$; provided that no more than one of $R_3$ and $R_4$ can be $CF_2CF_3$;
$R_5$ is H or $C_1-C_3$ alkyl; or a pharmaceutically suitable acid addition salt thereof.

DETAILED DESCRIPTION OF THE INVENTION

The compounds useful in the practice of the method of the present invention are described and claimed in U.S. Pat. No. 4,348,404, issued Sept. 7, 1982. The present invention is based on the finding that these compounds are unexpectedly useful for the treatment of hypertension in mammals.

Compounds of Formula I preferred for use for their antihypertensive activity are those wherein one of $R_1$ and $R_2$ is

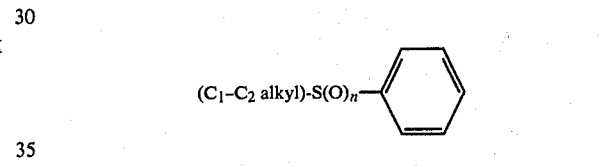

where $n = 0$–2. Especially preferred are those compounds where $n = 2$.

Specifically preferred compounds are:
(1) 4-(4-fluorophenyl)-5-(4-methylthiophenyl)-α,α-bis(trifluoromethyl)imidazole-2-methanamine.
(2) 4-(4-fluorophenyl)-5-(4-methylsulfinylphenyl)-α,α-bis(trifluoromethyl)imidazole-2-methanamine.
(3) 4-(4-fluorophenyl)-5-(4-methylsulfonylphenyl)-α,α-bis(trifluoromethyl)imidazole-2-methanamine.
(4) 4-phenyl-5-(4-methylthiophenyl)-α,α-bis(trifluoromethyl)imidazole-2-methanamine.
(5) 4-phenyl-5-(4-methylsulfonylphenyl)-α,α-bis(trifluoromethyl)imidazole-2-methanamine.

SYNTHESIS

Compounds of Formula I can be prepared by contacting an N-protected 4,5-diarylimidazole with a strong base, such as butyl lithium, in an inert solvent at low temperatures, followed by reaction with an appropriate fluorinated ketone imine.

The nature of the N-protecting group is such that it is stable to strong bases, but is acid-labile. Compounds of Formula I are obtained when the imidazole N-protecting group, P, is removed by an acidic reagent. Examples of useful acid labile protecting groups are 2-tetrahydropyranyl, benzyloxymethyl, methoxymethyl, methylthiomethyl, β-methoxyethoxymethyl, 2-tetrahydrofuranyl and α-ethoxyethyl.

The synthesis of N-protected 4,5-disubstituted imidazoles is described in U.S. Pat. No. 4,190,666; U.S. Pat. No. 4,182,769; and U.S. Pat. No. 4,159,338 which patents are herein incorporated by reference.

The reaction of a fluorinated ketone imine where $R_5=H$ with an N-protected 4,5-disubstituted imidazole requires the protection of the imine nitrogen atom with a group which can be later removed by acid. An example of a useful group is trimethylsilyl.

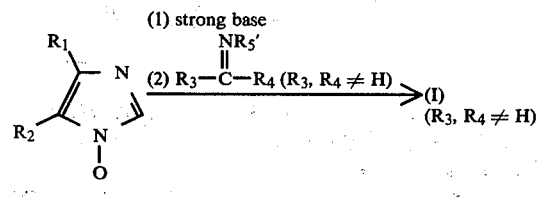

$R_5' = C_1$–$C_3$ alkyl or —$Si(CH_3)_3$

Compounds of Formula I of this invention with one of $R_3$ or $R_4=H$ can be prepared by a two-step process from 1-(4,5-diaryl-1H-imidazol-2-yl)polyfluoro-1-alkanones, by conversion to the oximes followed by reduction.

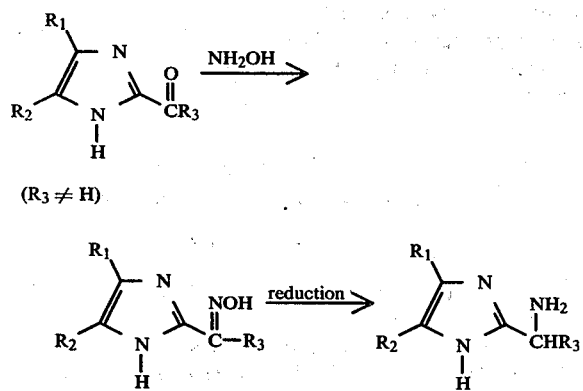

The 1-(4,5-diaryl-1H-imidazol-2-yl)polyfluoro-1-alkanones can be prepared from the corresponding N-protected 4,5-diaryl-1H-imidazoles by treatment with a strong base, such as n-butyl lithium, in an inert solvent at low temperature, followed by a fluorinated acid anhydride or an N,N-disubstituted fluorinated acid amide, followed by removal of the N-protecting group.

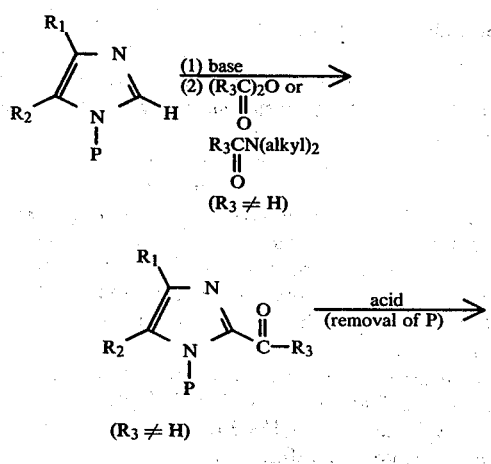

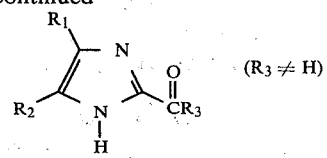

The oximes can be prepared by heating the polyfluoro-1-alkanones in the presence of hydroxylamine hydrochloride and a base (such as an alkali metal acetate, alkoxide, hydroxide or carbonate) in a polar solvent such as ethanol.

The reduction of the oxime is carried out by catalytic hydrogenation or by metal hydride reduction. Preferred conditions involve the use of lithium aluminum hydride in an ether solvent, such as diethyl ether or tetrahydrofuran at room temperature to the boiling point of the solvent.

A similar procedure used in the preparation of 1-phenyl-2,2,2-trifluoroethylamine hydrochloride has been described in the literature [R. A. Shepard and S. E. Wentworth, *J. Org. Chem.*, 32, 3197 (1967)].

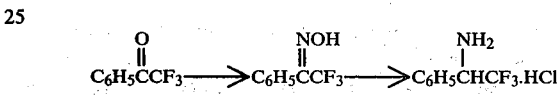

Compounds of Formula I of this invention with $R_5=C_1$–$C_3$ alkyl can be prepared by alkylation of the corresponding compounds where $R_5=H$. Alkylation can occur on either or both of the $NH_2$ or NH functionalities, depending on the conditions of the reaction. Often mixtures of alkylated products are obtained from which the desired alkylated products can be separated by conventional techniques. These alkylations can be conducted in the presence of a base, such as potassium carbonate, pyridine, triethylamine, potassium t-butoxide, sodium hydride or the like. An example of an alkylating agent is methyl iodide.

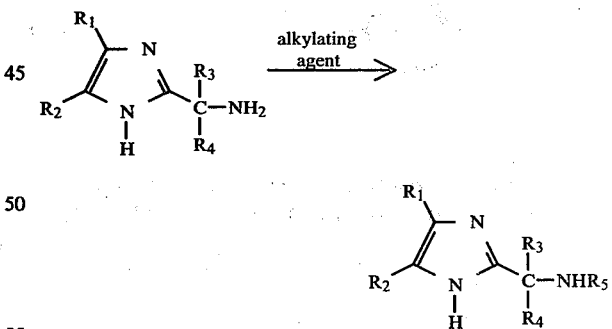

Pharmaceutically suitable salts of the compounds of Formula I can be prepared by treatment of the free base I with an appropriate acid.

In the following examples, all parts are by weight and temperatures are in degrees centigrade unless otherwise specified.

EXAMPLE 1

4-(4-Fluorophenyl)-5-(4-methylthiophenyl)-α,α-bis(trifluoromethyl)imidazole-2-methanamine Under an atmosphere of nitrogen, 1.6M n-butyl lithium in hexane (30 ml, 0.048 mole) was added dropwise to a solution of 1-(1-ethoxyethyl)-4-(4-fluorophenyl)-5-(4-methylthiophenyl)-1H-imidazole (10.0 g, 0.028 mole) and N,N,N',N'-tetramethylethylenediamine (3.9 g, 0.0336 mole) in tetrahydrofuran (150 ml) at −78° C. The mixture was stirred for 15 minutes at −78° C. and then N-(trimethylsilyl)hexafluoroacetone imine (11.0 g, 0.046 mole) was added dropwise at −78° C. The mixture was stirred for one hour at −78° C. and then allowed to warm to 0° C. A saturated aqueous solution of sodium bicarbonate (100 ml) was added dropwise while allowing the reaction mixture to warm to room temperature. The organic phase was separated and solvent removed in vacuo. Hydrochloric acid (2N; 100 ml) and ethanol (200 ml) were added to the residue and the mixture stirred overnight at room temperature. Ethanol was then removed under vacuum and the aqueous residue extracted with ether. The ether extracts were washed with water and then dried over magnesium sulfate. The ether solution was concentrated under reduced pressure and the residual oil placed on a column of dry silica gel; the product was eluted with hexane/ethyl acetate (1:1). Solvent was removed by evaporation in vacuo and the residue crystallized from 1-chlorobutane to afford 3.6 g (28%) of 4-(4-fluorophenyl)-5-(4-methylthiophenyl)-α,α-bis(trifluoromethyl)imidazole-2-methylamine, as colorless crystals, m.p. 150°–152°. IR: 3300 cm$^{-1}$ (NH$_2$). NMR: δ2.2 (s, 3H, CH$_3$); 3.0 (s, 2H, NH$_2$); 6.8–7.7 (m, 8H, aromatic).

Anal. Calcd. for C$_{19}$H$_{14}$N$_3$F$_7$S: C, 50.8; H, 3.12; N, 9.4. Found: C, 51.1; H, 3.1; N, 9.6.

EXAMPLE 2

4-(4-Fluorophenyl)-5-(4-methylsulfinylphenyl)-α,α-bis(trifluoromethyl)-1H-imidazole-2-methanamine A solution of 1.2 g (1.02 g net; 0.0060 mole) of 85% m-chloroperbenzoic acid in 120 ml of ether was dropped into a stirred solution 2.7 g (0.0060 mole) of 4-(4-fluorophenyl)-5-(4-methylthiophenyl)-α,α-bis(trifluoromethyl)-1H-imidazole-2-methanamine in 180 ml of ether in an ice-bath. After the mixture had stirred for one hour, the ice-bath was removed, and stirring was continued for 16 hours. The precipitate was filtered off and recrystallized from ethyl acetate to give 0.72 g (25%) of crystals, m.p. 231.5°–232.5°. (In larger, subsequent runs, yields of 65–70% of recrystallized product were obtained.) The mass spectrum (m/z 465) was consistent with the title compound.

Anal. Calcd. for C$_{19}$H$_{14}$F$_7$N$_3$OS: C, 49.03; H, 3.03; N, 9.03. Found: C, 49.3; H, 3.2; N, 9.3.

EXAMPLE 3

4-(4-Fluorophenyl)-5-(4-methylsulfonylphenyl)-α,α-bis(trifluoromethyl)-1H-imidazole-2-methanamine A. Preparation from Sulfoxide To a stirred solution of 2.4 g (0.0052 mole) of 4-(4-fluorophenyl)-5-(4-methylsulfinylphenyl)-α,α-bis(trifluoromethyl)-1H-imidazole-2-methanamine in 200 ml of methanol cooled in an ice-bath was added portionwise 9.2 g (0.015 mole) of Oxone ® (2KHSO$_5$•KHSO$_4$•K$_2$SO$_4$, available from Alfa Products). When addition was complete, the ice-bath was removed, and the mixture was stirred at ambient temperature for 16 hours.

The methanol was removed by evaporation, and the residue was distributed between ethyl acetate and water. The ethyl acetate layer was separated, washed (water), dried (MgSO$_4$), and evaporated to give 2.6 g of residue. Recrystallization from 1,2-dichloroethane gave 1.5 g (60%) of crystals, m.p. 210.5°–212.5°. The structure was confirmed by the NMR and IR spectra: $^1$H NMR (d$_6$-DMSO) δ3.20 (s, 3H, CH$_3$); 3.60 (s, 2H, NH$_2$); 7.0–8.0 (m, 3H, aromatic protons); 13.03 ppm (s, 1H, NH); IR 1310 cm$^{-1}$ (—SO$_2$—).

Anal. Calcd. for C$_{19}$H$_{14}$F$_7$N$_3$O$_2$S: C, 47.40; H, 2.93; N, 8.73. Found: C, 47.0; H, 2.8; N, 8.7.

B. Preparation from Methylthiophenylimidazole compound

To a stirred solution of 7.18 g (0.016 mole) of 4-(4-fluorophenyl)-5-(4-methylthiophenyl)-α,α-bis(trifluoromethyl)-1H-imidazole-2-methanamine in 200 ml of methanol cooled in an ice-bath was added portionwise 24.58 g (0.040 mole) of Oxone ® (see part A). The ice-bath was removed, and the mixture was stirred at ambient temperature for 16 hours. The solid was removed by filtration and discarded. The filtrate was evaporated to remove methanol, and the residue was treated as in part A. Recrystallization gave 5.9 g (77%) of crystals, m.p. 211.5°–213°. Thin layer chromatography on silica gel using 60:25:15 toluene-ethyl acetate-methanol showed a single spot with the same retention time as the product from part A (R$_f$0.53).

EXAMPLE 4

4-(4-Fluorophenyl)-5-(4-methoxyphenyl)-α,α-bis(trifluoromethyl)-1H-imidazole-2-methanamine To a cooled (−78° C.) solution of 1-(1-ethoxy-ethyl)-4-(fluorophenyl)-5-(4-methoxyphenyl)-1H-imidazole (5.0 g, 14.8 mmoles) and tetramethylethylenediamine (2.60 ml, 17.0 mmoles) in 75 ml of tetrahydrofuran was added 12.1 ml of 2.1M n-butyl lithium dropwise. The mixture was stirred for 15 minutes at −78° C., and then N-(trimethylsilyl)hexafluoroacetone imine (5.84 g, 24.6 mmoles) was added dropwise. After stirring for an additional hour at −78° C., the mixture was warmed to 0° C. Then, 55 ml of saturated sodium bicarbonate was added dropwise and the reaction mixture was brought to room temperature. The organic layer was separated and the solvent removed in vacuo. The residue was stirred overnight with a mixture of 110 ml of ethanol and 55 ml of 2N hydrochloric acid. The ethanol was removed under vacuum. The aqueous residue was extracted thoroughly with ether, dried over anhydrous magnesium sulfate and concentrated to dryness to afford 5.42 g (84%) of crude product. The residual oil was chromatographed on silica gel eluting with ether/hexane (1:4). The product fractions were recrystallized from butyl chloride/hexane to give 3.3 g (51.5%) of the title compound as white crystals, m.p. 123°–124° C.

Anal. Calcd. for C$_{19}$H$_{14}$F$_7$N$_3$O: C, 52.66; H. 3.23; N, 9.7. Found: C, 52.5; H, 3.4; N, 9.4

MS: m/z 433.

TABLE 1

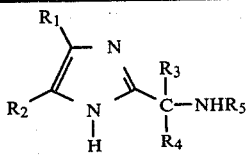

| Ex. | R₁ | R₂ | R₃ | R₄ | R₅ | m.p. (°C.) | Yield (%) |
|---|---|---|---|---|---|---|---|
| 1 | 4-FC₆H₄ | 4-CH₃SC₆H₄ | CF₃ | CF₃ | H | 150–152 | 28 |
| 2 | 4-FC₆H₄ | 4-CH₃SOC₆H₄ | CF₃ | CF₃ | H | 231.5–232.5 | 25 |
| 3 | 4-FC₆H₄ | 4-CH₃SO₂C₆H₄ | CF₃ | CF₃ | H | 211.5–213 | 77 |
| 4 | 4-FC₆H₄ | 4-CH₃OC₆H₄ | CF₃ | CF₃ | H | 123–124 | 52 |
| 5 | C₆H₅ | 4-CH₃SC₆H₄ | CF₃ | CF₃ | H | 115–117 | 64 |
| 6 | C₆H₅ | 4-CH₃SO₂C₆H₄ | CF₃ | CF₃ | H | 200.5–202 | 74 |
| 7 | C₆H₅ | 4-CH₃SO₂C₆H₄ | CF₃ | CF₂Cl | H | | |
| 8 | 4-FC₆H₄ | 4-CH₃SO₂C₆H₄ | CF₃ | CF₃ | CH₃ | | |
| 9 | 4-ClC₆H₄ | 4-CH₃SO₂C₆H₄ | CF₃ | CF₃ | H | | |

DOSAGE FORMS

The compounds of this invention can be administered in the treatment of hypertension according to the invention by any means that effects contact of the active ingredient compound with the site of action in the body of a warm-blooded animal. For example, administration can be parenteral (i.e., subcutaneous, intravenous, intramuscular, or intraperitoneal) or oral.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily oral dosage of active ingredient compound will be from about 0.05 to 100 milligrams per kilogram of body weight. Ordinarily, from 0.2 to 60, and preferably 0.4 to 40, milligrams per kilogram per day in one or more applications per day is effective to obtain desired results. For the more potent compounds of the invention, e.g., 4-(4-fluorophenyl)-5-(4-methylsulfonylphenyl)-α,α-bis(trifluoromethyl)imidazole-2-methanamine, the daily dosage ranges are from about 0.05–30 mg/kg, preferably 0.5–30 mg/kg, and more preferably 0.5–20 mg/kg.

Dosage forms (compositions) suitable for internal administration contain from about 0.1 milligrams to about 500 milligrams of active ingredient per unit. In this pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules can contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 50 milligrams of the active ingredient. The capsules are washed and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 27.5 milligrams of lactose. Appropriate coatings may be applied to increase palatability or delay absorption.

Injectable

A parenteral composition suitable for administration by injection is prepared by stirring 1.5% by weight of active ingredient in 10–60% by volume of co-solvents, like propylene glycol in water. The resultant solution can be sterilized by filtration.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by dissolving 1% by weight of active ingredient in sodium chloride injection U.S.P. XX and adjusting the pH of the solution to between 6 and 7. The solution can be sterilized by filtration.

Utility

Rat Tests

The antihypertensive activities of the compounds of this invention are evidenced by tests conducted in hypertensive rats. In some tests, rats are made hypertensive by subcutaneous implantation of pellets of desoxycorticosterone acetate (DOCA) and by giving the rats saline solution to drink essentially according to the method described by Sturtevant, *Annals of Internal Medicine*, 49, 1281 (1958). In other tests, spontaneously hypertensive rats are used. Graded dose levels of the test compound are administered orally (p.o.) or interperitoneally (i.p.) to groups of 8 hypertensive rats. The compound is prepared in an aqueous Methocel ® methyl cellulose—Tween ® 80 polyoxyethylene(20)-sorbitan monooleate vehicle and administered at a volume to body weight ratio of 5.0 ml/kg. Hypertensive rats receiving the aqueous vehicle by the same route serve as controls for each test. At various intervals of time after treatment the systolic arterial blood pressure of each rat is determined by modification of the microphone-manometer technique [Friedman, M. and Freed, S. C., *Proc. Soc. Exp. Biol. and Med.*, 70, 670 (1949)]. That dose of compound which produces a reduction in blood pressure of 30 mm mercury (mm Hg) when compared to the mean systolic arterial blood pressure of the control animals is then determined ($ED_{30}$).

The compounds of Examples 1 through 6 are effective in lowering blood pressure in DOCA-hypertensive and/or spontaneously hypertensive rats as shown in Table 2. All compounds are effective orally except for the compound of Example 4 which is active after intraperitoneal administration.

Dog Tests

Indwelling arterial and venous cannulae were implanted into normotensive mongrel dogs under anesthesia. On test days, arterial blood pressure was recorded through a cannula and recorded on a Grass Polygraph. After a 30-minute stabilization period, a test compound was administered through the venous cannula in 0.25% methocel vehicle. Blood pressure was recorded continuously for an additional 6 hours. Comparative hypotensive effects for the compounds of Examples 1, 2, and 3 are given in Table 2. The $ED_{30}$ value in this table is that dose required to reduce mean arterial blood pressure 30 mm Hg from the control level.

Monkey Tests

The compound of Example 3 was separately administered orally and intravenously to the monkey. By oral administration, at 50 mg/kg, it did not lower blood pressure. By intravenous administration, at 30 mg/kg, an almost immediate reduction in blood pressure of 37 mm Hg resulted. The compound of Example 1, administered orally at 20 mg/kg for 2 days, did not lower blood pressure.

It is believed that the compound of Example 1 would provide control of blood pressure in dogs and monkeys if tested under different conditions. Compound 1 was found effective in reducing blood pressure in the rat.

TABLE 2

| | $ED_{30}$ - mg/kg | | | | | |
|---|---|---|---|---|---|---|
| | DOCA-rat | | SHR | Dog | | Monkey | |
| Ex. | p.o. | i.p. | p.o. | p.o. | i.v. | p.o. | i.v. |
| 1 | 4.6 | | 11 | | inactive at 10 | inactive at 20 | |
| 2 | | | 25 | | ~20 | | |
| 3 | | | 2.8 | | 20 | inactive at 50 | <30 |
| 4 | >50 | 28 | | | | | |
| 5 | | | 4.6 | inactive at 50 | | | |
| 6 | | | 6.4 | inactive at 50 | | | |

What is claimed is:

1. A method of treating hypertension in a mammal which comprises administering to the mammal in need of said treatment an effective antihypertensive amount of a compound of Formula I:

Formula I

[Chemical structure: pyrazole ring with $R_1$ on N, $R_2$ attached, NH, and C($R_3$)($R_4$)—NHR$_5$ group]

wherein $R_1$ and $R_2$ independently are 2-pyridyl, 3-pyridyl, 4-pyridyl or

[phenyl ring with X and Y substituents]

where
 X = H, F, Cl, Br, $C_1$–$C_2$ alkyl, $C_1$–$C_2$ alkoxy, di($C_1$–$C_2$ alkyl)amino, ($C_1$–$C_2$ alkyl)S(O)$_n$, or NO$_2$, where n = 0, 1 or 2;
 Y = H, F or Cl; provided when Y = F or Cl, then X must be F or Cl;
 further provided that (1) one of $R_1$ and $R_2$ must be ($C_1$–$C_2$ alkyl)S(O)$_n$—[phenyl]— or -continued

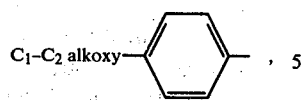, and (2) only one of $R_1$ and $R_2$ can be selected from the group consisting of 2-pyridyl, 3-pyridyl, 4-pyridyl, $(C_1-C_2 \text{ alkyl})S(O)$

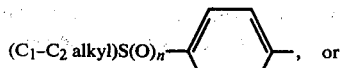, or

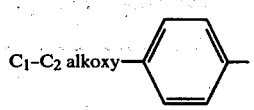, $R_3$ and $R_4$ independently $= CF_3$, $CF_2H$, $CF_2Cl$, $CFCl_2$ or $CF_2CF_3$; provided that no more than one of $R_3$ and $R_4$ can be $CF_2CF_3$;

$R_5$ is H or $C_1-C_3$ alkyl;

or a pharmaceutically suitable acid addition salt thereof.

2. The method of claim 1 wherein one of $R_1$ and $R_2$ is

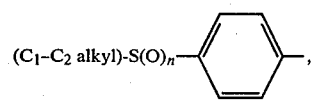, where n=0–2.

3. The method of claim 1 wherein one of $R_1$ and $R_2$ is

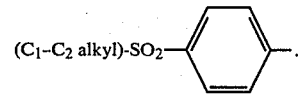.

4. The method of claim 1, 2, or 3 wherein at least one of $R_3$ and $R_4$ is $CF_3$.

5. The method of claim 1 wherein the compound is 4-(4-fluorophenyl)-5-(4-methylthiophenyl)-α,α-bis(trifluoromethyl)imidazole-2-methanamine.

6. The method of claim 1 wherein the compound is 4-(4-(fluorophenyl)-5-(4-methylsulfinylphenyl)-α,α-bis(trifluoromethyl)-1H-imidazole-2-methanamine.

7. The method of claim 1 wherein the compound is 4-(4-fluorophenyl)-5-(4-methylsulfonylphenyl)-α,α-bis(trifluoromethyl)-1H-imidazole-2-methanamine.

8. The method of claim 1 wherein the compound is 4-phenyl-5-(4-methylthiophenyl)-α,α-bis(trifluoromethyl)imidazole-2-methanamine.

9. The method of claim 1 wherein the compound is 4-phenyl-5-(4-methylsulfonylphenyl)-α,α-bis(trifluoromethyl)imidazole-2-methanamine.

* * * * *